United States Patent
Caillouette

[11] Patent Number: 5,998,161
[45] Date of Patent: Dec. 7, 1999

[54] AMINE DETECTION BY COLOR CHANGE, IN HUMAN BODY MOISTURE

[76] Inventor: James C. Caillouette, 685 Oak Knoll Cir., Pasadena, Calif. 91106

[21] Appl. No.: 09/161,545

[22] Filed: Sep. 28, 1998

[51] Int. Cl.[6] .............................. C12Q 1/04; C12Q 1/24; C12Q 1/00

[52] U.S. Cl. ................................. 435/34; 435/30; 435/4; 435/283.1; 435/287.1; 435/287.3; 422/50; 422/55; 422/68.1

[58] Field of Search ................................... 435/34, 30, 4, 435/283.1, 287.1, 287.3, 286.4; 422/50, 55, 68.1

[56] References Cited

U.S. PATENT DOCUMENTS

| | | | |
|---|---|---|---|
| 2,664,879 | 1/1954 | Hardy | 435/34 |
| 2,945,491 | 7/1960 | Gibbs | 435/34 |
| 3,013,656 | 12/1961 | Murphy, Jr. | 435/34 |
| 3,037,496 | 6/1962 | Melges | 435/34 |
| 3,117,569 | 1/1964 | Wegner | 435/34 |
| 3,319,621 | 5/1967 | Schwerin | 435/34 |
| 3,507,269 | 4/1970 | Berry | 435/34 |
| 3,509,872 | 5/1970 | Truhan | 435/34 |
| 3,777,743 | 12/1973 | Binard et al. | 435/34 |
| 4,010,738 | 3/1977 | Preti et al. | 435/34 |
| 4,409,182 | 10/1983 | Macklem | 435/34 |
| 4,457,313 | 7/1984 | Alter | 435/34 |
| 4,784,158 | 11/1988 | Okimoto | 435/34 |
| 4,820,259 | 4/1989 | Stevens | 435/34 |
| 4,862,899 | 9/1989 | Bucaro | 435/34 |
| 5,063,930 | 11/1991 | Nucci | 435/34 |
| 5,124,254 | 6/1992 | Hewlins et al. | 435/34 |
| 5,147,288 | 9/1992 | Schiavo | 435/34 |
| 5,425,377 | 6/1995 | Caillouette | 435/34 |
| 5,660,790 | 8/1997 | Lawrence et al. | 435/34 |
| 5,664,579 | 9/1997 | Caillouette | 435/34 |
| 5,738,634 | 4/1998 | Caillouette | 435/34 |
| 5,762,614 | 6/1998 | Caillouette | 435/34 |
| 5,782,801 | 7/1998 | Caillouette | 435/34 |

OTHER PUBLICATIONS

Webster's II Dictionary, p. 261, 1994.
"Vulvovaginitis", Ronald M. Meltzer, vol. 1, Chapter 37, 1994, Month not available.
"Urinary Incontinence And Related Urogenital Symptoms In Elderly Women", Ulla Molander, Scandinavian Association of Obstetricians and Gynecologists, Supplement 158, vol. 72, 1993, Month not available.
"Estrogen Deprivation And Vaginal Function In Postmenopausal Women", James P. Semmens, MD, Gorm Wagner, MD, 1982, Month not available.
"The Estradiol Vaginal Ring —A Study of Existing Clinical Data" Gloria Bachmann, Maturitas 22 Suppl. (1995) S21–S29, 1995, Month not available.
"Estrogens and the Urogenital Tract", Peter Smith, Dept. of Obstetrics & Gynecology, University Hospital, S–751 85 Uppsala, Sweden, 1993, Month not available.
"Nonspecific Vaginitis —Diagnostic Criterial and Microbial and Epidemiologic Associations", Richard Amsel, MD et al, The American Journal of Medicine, vol. 74, Jan., 1983.
"Biochemical Diagnosis of Vaginitis: Determination of Diamines in Vaginal Fluid", Kirk C.S. Chen et al, The Journal of Infectious Diseases, vol. 145, No. 3, Mar., 1982.
"Amine Content of Vaginal Fluid from Untreated and Treated Patients with Nonspecific Vaginitis", Kirk C.S. Chen et al, The American Society For Clinical Investigation, Inc., vol. 63, May, 1979, pp. 828–835.

Primary Examiner—Louise N. Leary
Attorney, Agent, or Firm—William W. Haefliger

[57] ABSTRACT

The method of detecting pathogenic bacteria, which includes providing a moisture receiver, onto which moisture containing an amine or amines is receivable, the amine or amines associated with the presence of pathogenic bacteria; providing a reactant which changes color upon contact with the amine or amines, and contacting the reactant with moisture at the receiver, whereby a change in color at the receiver indicates the presence of pathogenic bacteria in moisture.

39 Claims, 2 Drawing Sheets

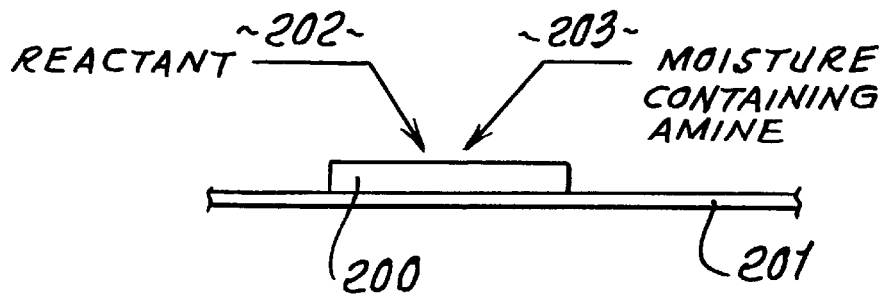
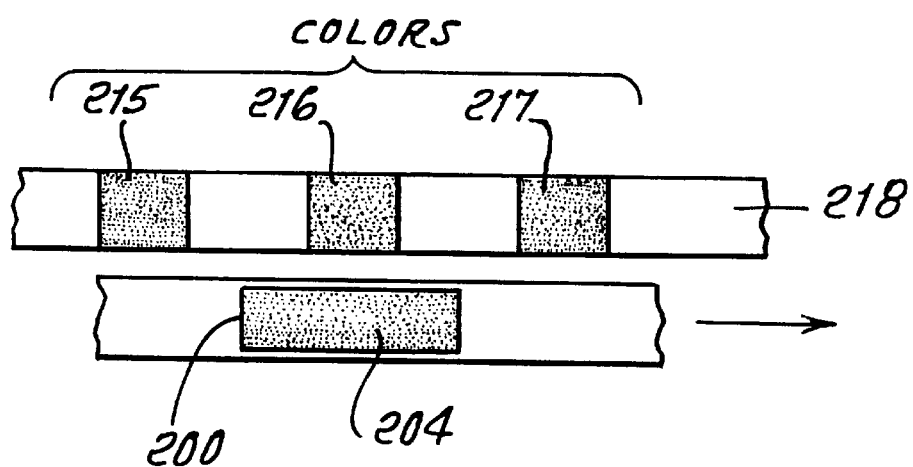
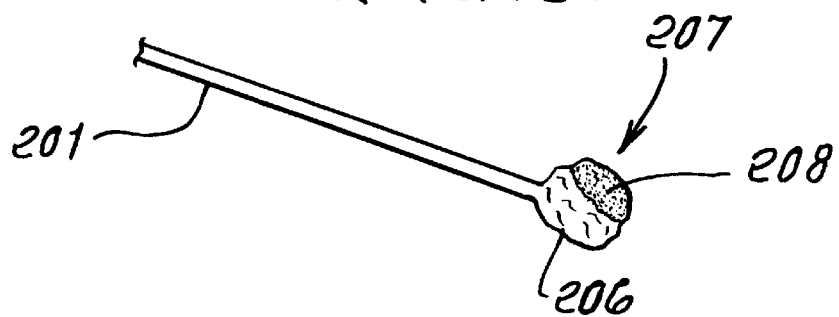

1

AMINE DETECTION BY COLOR CHANGE, IN HUMAN BODY MOISTURE

BACKGROUND OF THE INVENTION

This invention relates generally to detection of bacteria in moisture that contains an amine or amines, and more particularly to method and apparatus for easily and quickly, by color change, testing for the presence of bacteria in moisture samples as from the vagina, or from other sources.

There is need for simple, easily used apparatus, and easily performed methods, for reliably and quickly obtaining indications of bacteria, as for example pathogenic bacteria, in moisture samples, for example which contain an amine or amines, such as certain diamine or diamines. There is also need for simple, effective methods which visually provide such indications. Prior apparatus and techniques were cumbersome, difficult to interpret, and lacked the unusual advantages disclosed herein.

SUMMARY OF THE INVENTION

It is a major object of the invention to provide improvements in method and apparatus meeting the above needs. Basically, the method of the invention includes the following steps:

a) providing a moisture receiver, onto which moisture containing an amine or amines is receivable, the amine or amines associated with the presence of pathogenic bacteria, b) providing a reactant which changes color upon contact with an amine or amines, c) and contacting the reactant with moisture at the receiver, d) whereby a change in color at the receiver indicates the presence of pathogenic bacteria in the moisture.

As will be seen, the amine or amines are typically selected from the group putrecine and cadaverine. The reactant itself typically includes the indicator, and it may be carried by the receiver or applied to the receiver, in such manner that color change is readily observable. For example, the reactant may be in powder or other distributed state or form at the receiver, or it may be in liquid form and applied as by spraying or flowing onto the receiver. The indicator is typically selected from the group that includes Bromocresol Green, Bromocresol Purple, Nitrazine Yellow, Bromophenol Blue, and others which function similarly. The moisture at the receiver typically consists of human body moisture, the source of which may be a wound, or vaginal moisture. The receiver is typically porous to such moisture, such as a bandage or surgical dressing.

The present invention eliminates need for rubbing of retrieved moisture as onto a solid state reactant surface located for example on an auxiliary plate, whereby the present invention substantially simplifies the testing method and equipment employed to detect the presence of pathogenic bacteria as in the vagina. The present invention also eliminates need for a "whiff" test or odor test for pathogenic bacteria, as is commonly in use.

Another object is to provide the receiver in the form of a swab or other porous device or on a carrier that is manipulable for control of moisture deposition on the receiver for contact with the reactant to produce color change.

The reactant may include an alkali and a color change indicator, and may be provided in first and second layer form on the receiver, as for example i) a first layer containing the alkali, ii) a second layer containing the color change indicator, such layers being superimposed. The reactant is typically selected from the group that includes sodium aluminate, magnesium hydroxide, and sodium carbonate. A transparent porous cover layer may be provided on the first and second layers, and adapted to pass the amine containing moisture into contact with the layers.

These and other objects and advantages of the invention, as well as the details of an illustrative embodiment, will be more fully understood from the following specification and drawings, in which:

DRAWING DESCRIPTION

FIG. 1 is a view showing a receiver and received reactant and moisture;

FIG. 2 is a plan view of the FIG. 1 receiver, after color change, and color testing;

FIG. 3 is a view like FIG. 1, but showing a receiver swab, and color change in response to applied reactant and moisture;

DETAILED DESCRIPTION

Figure 4:
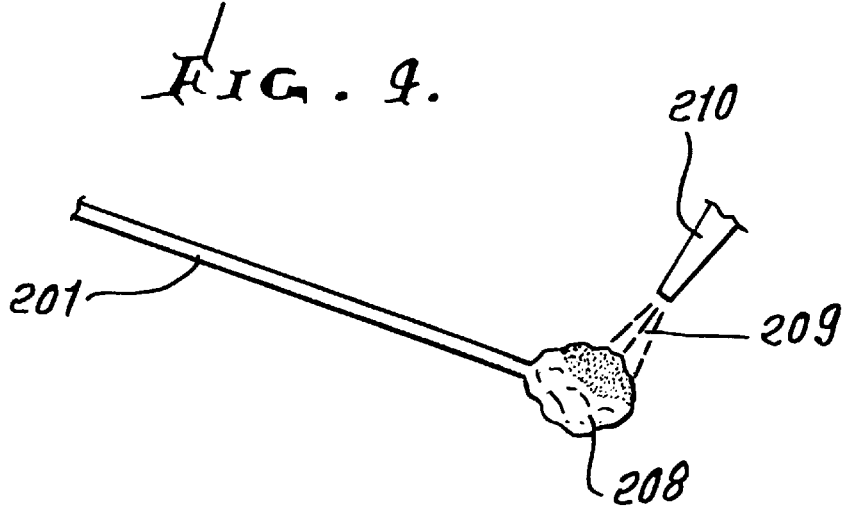
FIG. 4 is a view like FIG. 3, showing reactant spray onto the swab.

FIGS. 1 and 2 illustrate a method of detecting pathogenic bacteria. The steps of the preferred method include a) providing a moisture receiver, onto which moisture containing an amine or amines is receivable, said amine or amines associated with the presence of pathogenic bacteria, b) providing a reactant which changes color upon contact with said amine or amines, c) and contacting said reactant with said moisture at the receiver, d) whereby a change in color at the receiver indicates the presence of pathogenic bacteria in said moisture.

As shown, the receiver 200 may advantageously comprise a porous body which may or may not be mounted or carried as at one end of a carrier stick 201. The color changing reactant may be applied to or incorporated on, or in the interstices of the receiver. FIG. 1 shows the reactant being applied at 202 to the receiver. Amine carrying moisture is applied at 203 to the receiver. When the reactant is contacted by amine carrying moisture, a change in color at the receiver indicates the presence of pathogenic bacteria, such color change indicated by surface shading at 204 on receiver 200, in FIG. 2. The reactant may typically consist of an alkali such as liquid (aqueous) potassium hydroxide, powder form sodium aluminate, or others as referred to above, and a color change indicator, which changes color in the presence of the alkali and the amine, or diamine, such as putrecine and/or cadaverine. The reactant may be distributed as in powder form or on the receiver. The receiver is typically manipulated to control contact of in situ reactant with moisture received on the receiver, as for example in the vagina to receive vaginal moisture.

In a modified form of the method, the reactant is brought into contact with the receiver on which vaginal moisture has been deposited in response to swabbing, the receiver being in the form of a swab. FIG. 3 shows a swab 206 free of reagent during swabbing, but on which vaginal moisture has been deposited. Reagent is brought into contact with the moisture on the swab, as indicated by the arrow 207. The shaded area 208 indicates a change in color at the receiver or swab, showing presence of pathogenic bacteria. Arrow 207 may represent placement of the reactant onto the swab.

Figure 5:
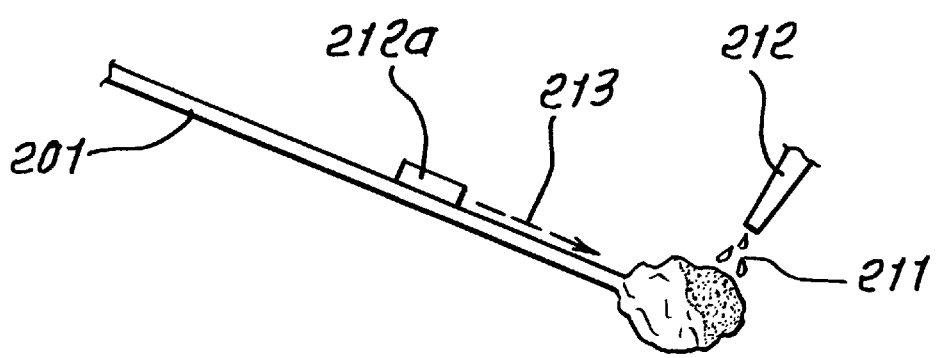
FIG. 5 is a view like FIG. 4, reactant liquid flowing onto the swab.

Another example of such contacting is spraying of the reactant in sprayable form onto the swab, as shown at 208 in FIG. 4. The spray 209 discharges from a spraying device 210. A further example of such contacting is flowing of the reactant, in fluid form, indicated by arrow 211 in FIG. 5, onto the swab, to contact vaginal moisture. The fluid reactant discharges from a fluid container 212, which may for example be free of the carrier stick 201, or which maybe mounted on the carrier stick as at 212*a*. Flow from 212*a* is indicated at 213.

FIG. 2 also shows an optimal confirmation step of obtaining a visual comparison of the color changed zone 204 on the receiver with color, or different colors, or color shades as at 215–217 on a carrier 218. Color 216 may indicate presence of putrecine; color 217 may indicate presence of cadaverine; and color 215 may be another color or color shade close to but different from 216 and 217, and so indicating absence of putrecine or cadaverine, when compared side-by-side with the color on the receiver 200, at 204.

In FIG. 1, the receiver may be a porous body, as for example a bandage, or dressing, or swab, as described above. Body moisture of any type may be applied to the receiver, for testing for presence of pathogenic bacteria. In general, body moisture plus alkali plus color indicator produce a color change of the indicator when pathogenic bacteria are present in said moisture producing amines such as putrecine and cadaverine. Such a color test obviates need for a so-called "whiff" test sometimes deemed objectionable.

Figure 6:
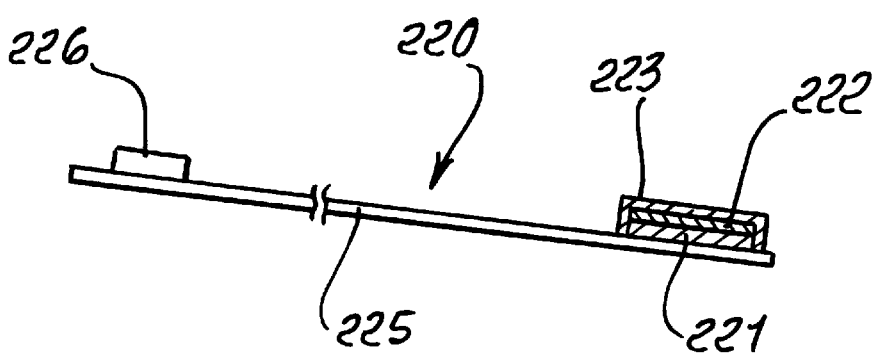
FIG. 6 is a view like FIG. 1, but showing a sandwich assembly of components.

In FIG. 6, a particularly advantageous test apparatus 220 is shown. It includes an elongated carrier 225 which is manually manipulable; a thin layer 221 on the stick and comprising a color indicator; a second thin layer 222 overlying layer 221 and comprising alkali or alkali powder (KOH, or sodium aluminate, or another or others as referred to above, for example); and porous and transparent cover layer 223 overlying 222 and 221. The cover layer may consist of clear, porous, hydrophobic synthetic polymer material, which passes applied moisture to contact layers 221 and 222.

The carrier 225 may carry other test elements, indicated at 226, for testing other human or animal body conditions, or body fluid conditions, such as pH level.

I claim:

1. A method of detecting pathogenic bacteria, which includes
    a) providing a moisture receiver, onto which moisture containing an amine or amines is receivable, said amine or amines associated with the presence of pathogenic bacteria,
    b) providing a reactant or reactants to produce a color change upon contact with said amine or amines,
    c) and contacting said reactant or reactants with said moisture at the receiver,
    d) whereby a change in color at the receiver indicates the presence of pathogenic bacteria in said moisture,
    e) said reactant or reactants comprising a color change indicator and an alkali.

2. A method of detecting pathogenic bacteria, which includes
    a) providing a moisture receiver, onto which moisture containing an amine or amines is receivable, amine or amines associated with the presence of pathogenic bacteria,
    b) providing a reactant or reactants which cause change in color upon contact with said amine or amines,
    c) and contacting said reactant or reactants with said moisture at the receiver,
    d) whereby a change in color at the receiver indicates the presence of pathogenic bacteria in said moisture,
    e) and wherein one reactant is an indicator selected from the group consisting essentially of Bromocresol Green, Bromocresol Purple, Nitrazine Yellow, Bromophenol Blue, and equivalents.

3. A method of claim 1 wherein said amine or amines is or are selected from the group putrecine and cadaverine.

4. A method of detecting pathogenic bacteria, which includes
    a) providing a moisture receiver, onto which moisture containing an amine or amines is receivable, said amine or amines associated with the presence of pathogenic bacteria,
    b) providing a reactant or reactants which cause change in color upon contact with said amine or amines,
    c) and contacting said reactant or reactants with said moisture at the receiver,
    d) whereby a change in color at the receiver indicates the presence of pathogenic bacteria in said moisture,
    e) said amine or amines being from the group putrecine and cadaverine,
    f) and wherein one reactant is a substance selected from the group that consists essentially of liquid potassium hydroxide, powder form sodium aluminate, magnesium hydroxide and sodium carbonate.

5. The method of claim 1 wherein the reactant is carried by the receiver.

6. The method of claim 1 wherein the reactant is applied to the receiver.

7. A method of detecting pathogenic bacteria which includes
    a) providing a moisture receiver, onto which moisture containing an amine or amines is receivable, said amine or amines associated with the presence of pathogenic bacteria,
    b) providing a reactant or reactants which cause change in color upon contact with said amine or amines,
    c) and contacting said reactant or reactants with said moisture at the receiver,
    d) whereby a change in color at the receiver indicates the presence of pathogenic bacteria in said moisture,
    e) and wherein the reactant or reactants is or are applied to the receiver by spraying.

8. A method of detecting pathogenic bacteria, which includes
    a) providing a moisture receiver, onto which moisture containing an amine or amines is receivable, said amine or amines associated with the presence of pathogenic bacteria,
    b) providing a reactant or reactants which cause change in color upon contact with said amine or amines,
    c) and contacting said reactant or reactants with said moisture at the receiver,
    d) whereby a change in color at the receiver indicates the presence of pathogenic bacteria in said moisture,
    e) and wherein the reactant or reactants is or are applied to the receiver by flowing.

9. A method of detecting pathogenic bacteria, which includes a) providing a moisture receiver, onto which moisture containing an amine or amines is receivable, said amine or amines associated with the presence of pathogenic bacteria, b) providing a reactant or reactants which cause change in color upon contact with said amine or amines, c) and contacting said reactant or reactants with said moisture at the receiver, d) whereby a change in color at the receiver indicates the presence of pathogenic bacteria in the moisture, e) and wherein the reactant or reactants is or are in powder form at the receiver.

10. The method of claim 1 wherein said moisture consists of vaginal moisture.

11. The method of claim 1 wherein said receiver is provided to be porous to said moisture.

12. The method of claim 1 wherein said receiver is provided in the form of a swab.

13. The method of claim 10 including manipulating said receiver to control said contacting of reactant with vaginal moisture on the receiver.

14. The method of claim 10 including manipulating said reactant or reactants to control said contacting of the reactant or reactants with vaginal moisture on the receiver.

15. The method of claim 13 wherein said receiver is provided in the form of a swab.

16. The method of claim 15 including providing a stick on which the swab is carried, the stick being manipulated to manipulate the swab to control said contacting.

17. The method of claim 1 wherein the receiver is provided in the form of a swab.

18. The method of claim 17 including providing a stick on which the swab is carried.

19. The method of claim 17 including bringing the reactant onto contact with the swab to effect said contacting.

20. The method of claim 1 wherein said contacting is effected by placing the reactant into contact with the receiver.

21. The method of claim 1 wherein the receiver is provided in the form of one of the following:

i) a bandage, or ii) a surgical dressing, or iii) a porous device onto which human or animal body moisture is receivable.

22. The method of claim 1 wherein said color change indicator is selected from the group consisting essentially of Bromocresol Green, Bromocresol Purple, Nitrazine Yellow, Bromophenol Blue, and equivalents.

23. The method of claim 1 including providing said reactant in the form of a layer or layers, on the receiver.

24. The method of claim 1 including providing said reactant in the form of i) a first layer containing said alkali, and ii) a second layer containing said color change indicator, said layers being superimposed.

25. The method of claim 24 including providing a transparent porous cover over said first and second layers, and adapted to pass said moisture into contact with said layers.

26. The method of claim 24 including providing said receiver to include an elongated carrier on which said layers are carried.

27. The method of claim 25 including providing said receiver to include an elongated carrier on which said layers are carried.

28. The method of claim 1 including controlling said contacting of the reactant with said moisture, at the receiver.

29. Apparatus for detecting pathogenic bacteria in human or animal body moisture, comprising a) a moisture receiver onto which moisture containing an amine or amines is receivable, said amine associated with the presence of pathogenic bacteria, b) a reactant or reactants which cause change in color upon contact with said amine or amines, c) the reactant or reactants positioned for contact with moisture at the receiver, d) whereby a change in color at the receiver indicates the presence of pathogenic bacteria in said moisture, e) said reactant or reactants comprising a color change indicator and an alkali.

30. The apparatus of claim 29 wherein said receiver is in the form of a swab.

31. The apparatus of claim 29 wherein said reactant is carried by the receiver.

32. The apparatus of claim 29 wherein said reactant comprises an alkali and a color change indicator.

33. The apparatus of claim 29 including means for manipulating said receiver to control said contacting of the reactant with moisture at the receiver.

34. The apparatus of claim 29 including means for manipulating said reactant to control said contacting of the reactant with moisture at the receiver.

35. The apparatus of claim 33 wherein said receiver is provided in the form of a porous body.

36. The apparatus of claim 35 including a stick on which the porous body is carried, the porous body manipulable by the stick to control said contacting.

37. Apparatus for detecting pathogenic bacteria in human or animal body moisture, comprising a) a moisture receiver onto which moisture containing an amine or amines is receivable, said amine associated with the presence of pathogenic bacteria, b) a reactant or reactants which cause change in color upon contact with said amine or amines, c) the reactant or reactants positioned for contact with moisture at the receiver, d) whereby a change in color at the receiver indicates the presence of pathogenic bacteria in said moisture, e) and wherein said reactant or reactants is or are positioned proximate the receiver to flow into contact with the receiver.

38. Apparatus for detecting pathogenic bacteria in human or animal body moisture, comprising a) a moisture receiver onto which moisture containing an amine or amines is receivable, said amine associated with the presence of pathogenic bacteria, b) a reactant or reactants which cause change in color upon contact with said amine or amines, c) the reactant or reactants positioned for contact with moisture at the receiver, d) whereby a change in color at the receiver indicates the presence of pathogenic bacteria in said moisture, e) and wherein said reactant or reactants is or are contained by a spray device to be sprayed into contact with the receiver.

39. The apparatus of claim 29 wherein the reactant is in contact with the receiver.

* * * * *